US00PP30688P3

(12) United States Plant Patent
Schoone

(10) Patent No.: US PP30,688 P3
(45) Date of Patent: Jul. 9, 2019

(54) *PHALAENOPSIS* ORCHID PLANT NAMED 'TIGRIS'

(50) Latin Name: *Phalaenopsis hybrida*
Varietal Denomination: Tigris

(71) Applicant: Floricultura, Heemskerk (NL)

(72) Inventor: René Schoone, Assendelft (NL)

(73) Assignee: FLORICULTURA, Heemskerk (NL)

( * ) Notice: Subject to any disclaimer, the term of this patent is extended or adjusted under 35 U.S.C. 154(b) by 0 days.

(21) Appl. No.: 15/932,734

(22) Filed: Apr. 18, 2018

(65) Prior Publication Data

US 2018/0310450 P1 Oct. 25, 2018

Related U.S. Application Data

(60) Provisional application No. 62/487,867, filed on Apr. 20, 2017.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Annette H Para
(74) *Attorney, Agent, or Firm* — Sunit Talapatra

(57) ABSTRACT

A new and distinct *Phalaenopsis* plant named 'Tigris' particularly characterized by flowers which are purple/violet with a white mark in the center; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Tigris'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Tigris'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Tigris' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Tigris' originated from a cross made by the inventor in 2004 in Strengweg, Heemskerk, The Netherlands. The female or seed parent is the *Phalaenopsis* cultivar designated 'Carmen', unpatented. The male or pollen parent is the *Phalaenopsis* cultivar designated '(Brother Success x Ever Spring Rose)', unpatented. The new *Phalaenopsis* 'Tigris' was discovered and selected by the inventor as a single flowering plant within the progeny of the stated cross in a controlled environment in 2012 in Strengweg, Heemskerk, The Netherlands.

Asexual reproduction of the new *Phalaenopsis* cultivar by tissue culture (mericloning) was first performed in November, 2012 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Tigris', which in combination distinguish this *Phalaenopsis* as a new and distinct cultivar:

1. flowers which are purple/violet with a white mark in the center;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Tigris', the female parent 'Carmen' has larger flowers (about 10 cm) and is purple/violet. The male parent (Brother Success x Ever Spring Rose) has smaller flowers (about 8 cm) and is purple/violet with a white haze in the center, whereas the flowers of 'Tigris' are about 9 cm and purple/violet with a white haze in the center.

Presently, the commercial cultivar to which 'Tigris' can be meaningfully compared is 'Eternal Flame'. The flowers of 'Tigris' are darker purple/violet with a white mark at the center, whereas the flowers of 'Eternal Flame' are purple/violet with small white edges. Also the labellum differs in shape and the labellum of 'Eternal Flame' is darker in color.

BRIEF DESCRIPTION OF THE PHOTOGRAPHS

The accompanying photographs illustrate the overall appearance of the new *Phalaenopsis* 'Tigris' showing the colors as true as is reasonably possible with colored reproductions of this type. Colors in the photographs may differ slightly from the color values cited in the detailed botanical description, which accurately describe the color of 'Tigris'.

DETAILED BOTANICAL DESCRIPTION

Figure 1:
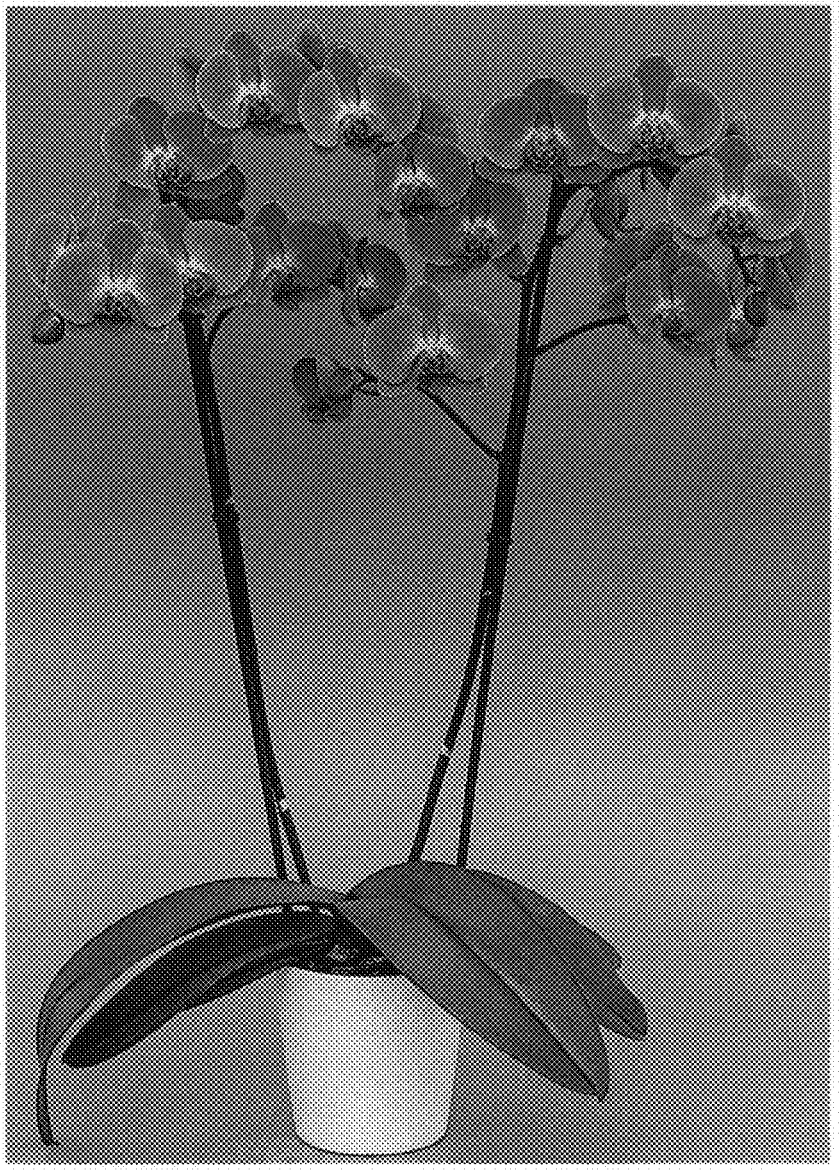
FIG. 1 shows a side view perspective of a typical flowering plant of 'Tigris' in a 12 cm pot, at 16 months of age.

The new *Phalaenopsis* cultivar 'Tigris' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Tigris' as grown in a greenhouse in Strengweg, Heemskerk, The Netherlands, under conditions which closely approximate those generally used in commercial practice. Initially, the ideal temperature to grow plants of 'Tigris' is 27° C. during the day and at night. Then, during the flowering phase of 'Tigris', the ideal growing temperature is 20-22° C. during the day and 18° C. at night. Light levels for growing 'Tigris' are a minimum of 5,000 lux and a maximum of 10,000 lux. A balanced fertilizer with level of 200 ppm N, 87 ppm P, 168 ppm K is applied. Duration of growth of 'Tigris' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Tigris' plants described is 12 months after potting.

Classification:
- *Botanical.*—*Phalaenopsis hybrida.*

Parentage:
- *Female or seed parent.*—*Phalaenopsis* cultivar designated 'Carmen', unpatented.
- *Male or pollen parent.*—*Phalaenopsis* cultivar designated (Brother Success x Ever Spring Rose), unpatented.

Propagation:
- *Type.*—Tissue culture.
- *Rooting habit and description.*—Fleshy; approximately 4 mm-8 mm wide and greyed/green in color (RHS 190A); freely branching. It takes 12 weeks for plants growing in tissue culture to initiate roots.

Plant:
- *Size at maturity.*—Height (from bottom of pot to highest flower): about 60 cm. Spread: about 50 cm.
- *Growth habit.*—Standard; green leaves (RHS N137A) and a relatively normal raceme.
- *Vigor.*—Moderate.
- *Crop time.*—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:
- *Quantity per plant.*—About 6-8 leaves are produced before flowering.
- *Arrangement and attachment.*—Half up/horizontal and on two sides.
- *Overall shape of leaf.*—Oval; the tip is blunt and asymmetric.
- *Texture* (*upper* & *underside*).—Smooth and leathery.
- *Pubescence.*—None.
- *Mature leaf length.*—About 18 cm.
- *Mature leaf width.*—About 7 cm.
- *Mature leaf thickness.*—About 2 mm.
- *Mature leaf color.*—Upper side: green (RHS N137A). Under side: green (RHS 137B) with a little brown at the edges (RHS 200A).
- *Leaf base.*—Acute.
- *Margin.*—Entire.
- *Venation.*—Pattern: parallel. Color of midvein: upper side: green (RHS N137A). under side: green (RHS 137D).

Inflorescence description:
- *Appearance.*—Upright to slightly pendant, racemose inflorescence with bilaterally symmetrical flowers that open in succession beginning with the lowermost flower.

Raceme:
- *Quantity per plant.*—About 2.
- *Number of flowers per raceme.*—About 8-16.
- *Length.*—About 35 cm.
- *Diameter.*—About 4 mm.

Peduncle:
- *Length.*—About 25 cm.
- *Diameter.*—About 4 mm.
- *Strength.*—Strong.
- *Aspect.*—Upright.
- *Texture.*—Glabrous and smooth.
- *Color.*—Green (RHS 137C) and brown (RHS 200A).
- *Buds.*—Height (from base to tip): about 25 mm. Diameter (at midpoint): about 20 mm. Shape: asymmetric oval. Color: red/purple (RHS 70A) with a yellow/green haze (RHS 145C). Orientation: same as flowers (forward facing).

Flowering time: For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

Flowering longevity: On the plant: about 4 to 6 months; lastingness of cut flowers: has not been observed.

Fragrance: No fragrance.

Flower:

*Rate of opening*.—Flowers fully opened about 2 to 3 days after petal and sepal separation.

*Orientation at opening*.—Slanted upward and outward.

Figure 2:
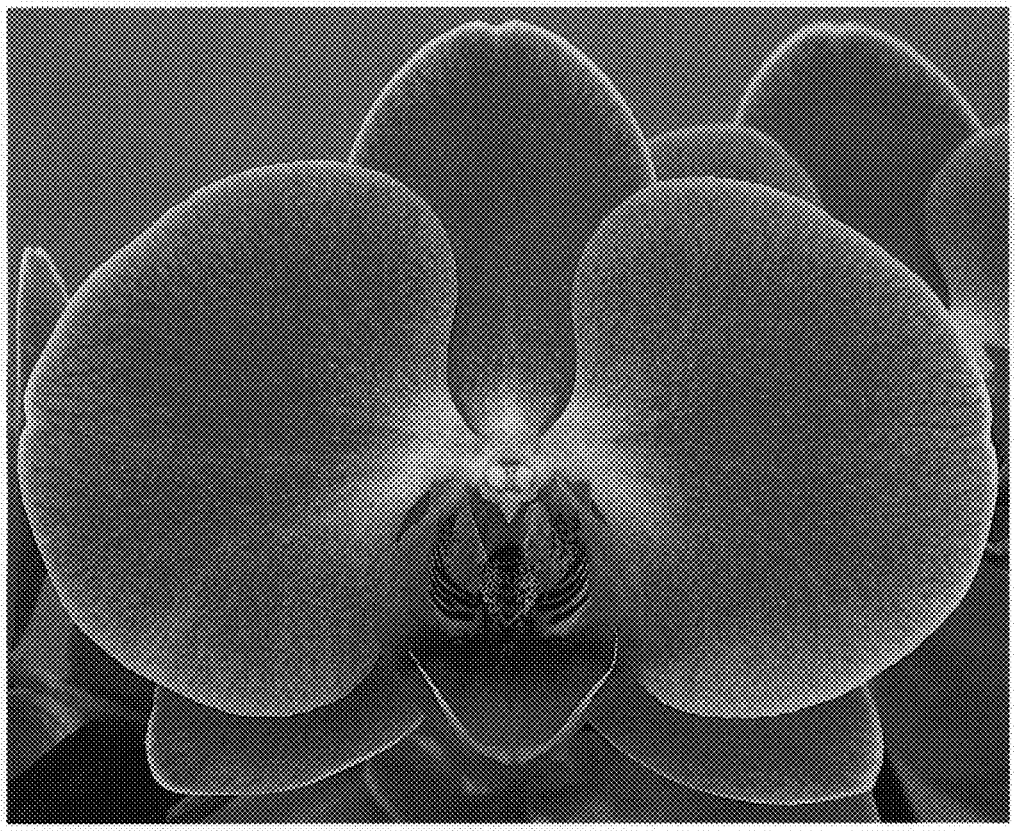
FIG. 2 shows a close-up view of the typical flower of 'Tigris'.
Figure 3:
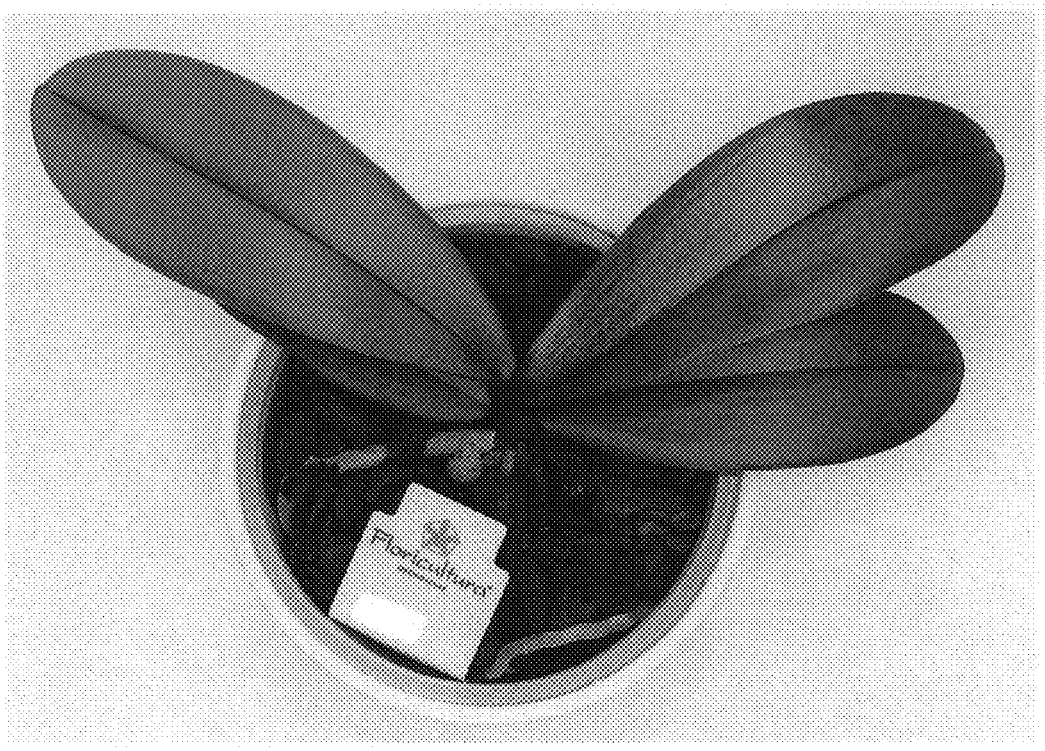
FIG. 3 shows a close-up view of the typical leaves of 'Tigris'.

*Shape*.—Typical shape of *Phalaenopsis*; see FIG. 2.

*Size* (*of single bloom*).—Height: about 80 mm. Diameter: about 90 mm.

*Quantity and arrangement*.—Three petals and three sepals that are trimerous, overlapping and arranged in 2 whorls. Petals are more pronounced than sepals.

Petals:

*Arrangement*.—Inner whorl comprises 3 petals: 2 lateral petals and a labellum.

2 *lateral petals*.—Overall shape: broadly ovate and weakly cupped. Apex: round. Margin: entire and weakly undulate. Base: broadly ovate. Length: about 55 mm. Width: about 40 mm. Texture: Upper surface: smooth and satiny. Under surface: smooth and satiny. Color (when fully opened): upper side: Main color is purple/violet (a combination of RHS N80A and RHS N80B). At the base a white mark (RHS NN155C) and some small white spots (RHS N155B). Also small white edges (RHS NN155D). Under side: purple violet (RHS N80B with some RHS N80C) with some white at the base (RHS NN155D). Labellum: Overall shape: 3-lobed with 2 prominent callosities at central junction of the lateral lobes and base of the midlobe. Lateral lobes of labellum fold upward about the column; the midlobe extends forward and is terminated by 2 appendages at the apex. Lateral lobes of the labellum are ovate in shape while the midlobe is triangular with a bump and a rib on it. Margin: entire and weakly undulate. Apex of the midlobe and lateral lobes: oval. Length midlobe: about 28 mm. Width midlobe (not flattened): about 25 mm. Length lateral lobe: about 22 mm. Width lateral lobe (not flattened): about 21 mm. Depth of tube created by lateral lobes of labellum: about 21 mm. Texture: Upper & under surface: smooth and satiny. Color (when fully opened): Midlobe, upper side: Main color is purple/violet (RHS N80A). At the base some yellow (RHS 9A) with some red/purple spots (RHS 59A). At the base, corners and the middle line red/purple (RHS 59A). Under side: Main color is purple/violet (RHS N80A). At the base some red/purple (RHS 59A) with a yellow haze (RHS 9A). Lateral lobes, upper side: Main color is purple/violet (combination of RHS N80B and RHS N80C). At the base white (RHS NN155D) with red/purple stripes (RHS 59A). Lower edge some red/purple (RHS 59A) with a yellow haze (RHS 9A). Under side: Main color is purple/violet (combination of RHS N80B and RHS N80C). At the base white (RHS NN155D) with a yellow haze (RHS 9A). Lower edge some red/purple (RHS 59A). Cirrhi: about 20 mm. color: purple/violet (RHS N80B) which runs into white (RHS N155C). Pestle (Callosities): Length: about 5 mm. Width (not flattened): about 5 mm. Color: yellow (RHS 9A) with red/purple stripes/spots (RHS 59A).

Sepals:

*Arrangement*.—Outer whorl comprises 3 sepals, one dorsal and two lateral sepals.

*Overall shape*.—Elliptical and weakly cupped.

*Margin*.—Entire and weakly undulate.

*Length*.—About 45 mm.

*Width*.—About 32 mm.

*Apex*.—Oval.

*Texture*.—Upper and under surface: smooth and satiny.

*Color* (*when fully opened*).—Upper side, dorsal: Main color is purple/violet (a combination of RHS N80A and RHS N80B). At the base white (RHS N155B) and some small white spots (RHS N155C). Lateral: Main color is purple/violet (a combination of RHS N80A and RHS N80B). At the base some white (RHS 155C) with a yellow/green haze (RHS 145D) with purple spots (RHS 77A). Under side, dorsal: Main color is purple/violet (a combination of RHS N80A and RHS N80B) with some purple/violet spots (RHS N80B) and some small violet edges (RHS 84D). Lateral: purple/violet (a combination of RHS N80A and RHS N80B) with at the base some white (RHS N155C) with a yellow/green haze (RHS 145D).

Pedicel:

*Length*.—About 4 cm.

*Diameter*.—About 3 mm.

*Texture*.—Glabrous and smooth.

*Color*.—White (RHS NN155D) which runs into red/purple (RHS 71A) with a yellow/green haze (RHS 145D).

Reproductive organs:

Arrangement: The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

Column:

*Length*.—About 12 mm.

*Diameter*.—About 5 mm.

*Color*.—Purple/violet (RHS N80B and RHS N80C) and white (RHS NN155C).

Pollinia:

*Quantity*.—Two.

*Diameter*.—About 4 mm.

*Color*.—Yellow/orange (RHS 23A).

Ovary:

*Length*.—About 4 mm.

*Diameter*.—About 3 mm.

*Color*.—White (RHS NN155D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Tigris', as illustrated and described herein.

* * * * *